United States Patent [19]

Behrstock

[11] 4,275,724

[45] Jun. 30, 1981

[54] ENDOTRACHEAL INTUBATION DEVICE

[76] Inventor: Barry Behrstock, 275 Victoria St., Costa Mesa, Calif. 92627

[21] Appl. No.: 25,905

[22] Filed: Apr. 2, 1979

[51] Int. Cl.$^3$ .......................................... A61M 25/00
[52] U.S. Cl. ................................. 128/207.14; 128/276
[58] Field of Search ............. 128/276, 207.14, 200.26, 128/204.18, 350 R, 350 V, DIG. 9, 349 R

[56] References Cited

U.S. PATENT DOCUMENTS

| | | | |
|---|---|---|---|
| 3,050,062 | 8/1962 | Ulmer | 128/276 |
| 3,322,126 | 5/1967 | Rusch et al. | 128/207.15 |
| 3,443,564 | 5/1969 | Oehmig | 128/207.14 |
| 3,538,918 | 11/1970 | Engelsher | 128/200.26 |
| 3,856,051 | 12/1974 | Bain | 128/204.18 |
| 3,913,565 | 10/1975 | Kawahara | 128/207.15 |
| 3,948,274 | 4/1976 | Zeldman | 128/207.1 X |
| 4,050,466 | 9/1977 | Koerbacher | 128/207.1 X |
| 4,052,989 | 10/1977 | Kline | 128/349 R |

FOREIGN PATENT DOCUMENTS 2013463  4/1970  France ................................. 128/204.18

Primary Examiner—Robert W. Michell
Assistant Examiner—J. L. Kruter
Attorney, Agent, or Firm—Richard H. Zaitlen

[57] ABSTRACT

An endotracheal intubation device which enables the user to simultaneously apply suction during the intubation process is disclosed. The device comprises a first elongated, flexible tube having an insertion tip at one end thereof designed for insertion into the nasopharnyx, orpharnyx and trachea of a newborn baby. A second elongated, flexible tube is slideably disposed about the first tube. The second tube has an insertion tip at one end thereof and grip means adjacent the other end. The second tube further has various means for shaping the second tube into a predetermined configuration such that the second tube and the first tube are both selectively retained in such configuration. By the use of the device of the present invention, the same suction device can be used to expedite the suction of material such as meconium from the oral, nasogastric and trachea region.

5 Claims, 5 Drawing Figures

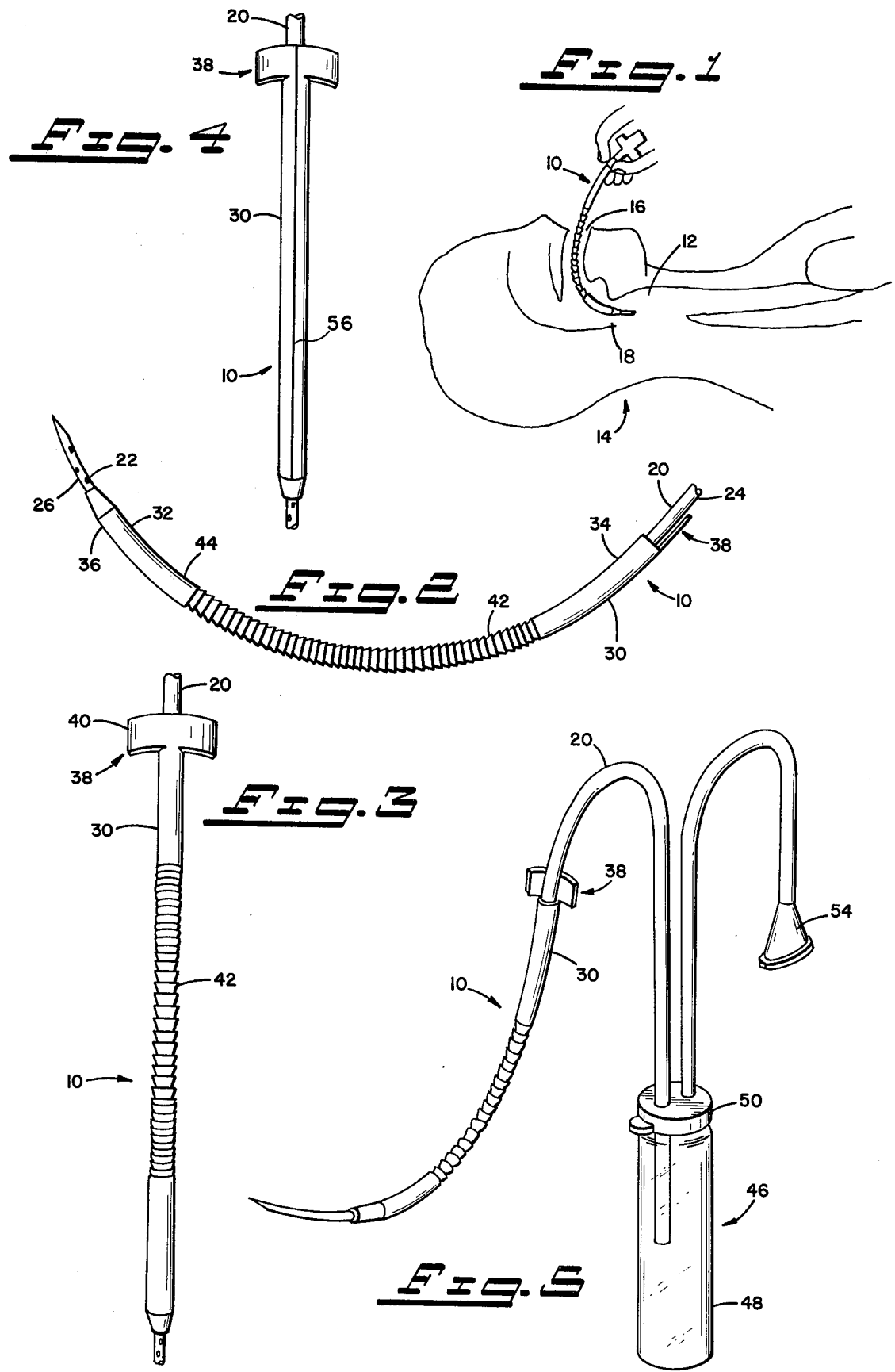

ENDOTRACHEAL INTUBATION DEVICE

BACKGROUND OF THE INVENTION

1. Field of the Invention

This invention relates to the field of medical devices, and more specifically, to an endotrachael intubation device.

2. Prior Art

The use of various-shaped tubing in the medical arts is well recognized. Generally, each tube is specifically configured so as to achieve a specific purpose. For example, U.S. Pat. Nos. 3,908,665 and 4,068,658 are directed to pharyngeal airways. These airways are formed by a specifically shaped tube which is inserted into the mouth and pharynx, and are designed for use in the practice of anesthesiology and resuscitation.

U.S. Pat. Nos. 3,948,274 and 4,050,466 are directed to endotracheal tubes of different configurations. These tubes are designed for insertion through an opening cut in the front of the throat or directly through the mouth and beyond.

Reference is also made to U.S. Pat. Nos. 3,982,546; 3,957,055; 3,894,540 and 3,169,528. Each of these references shows yet other tubing devices used in the medical arts.

While the above prior art devices may provide a specific advantage which is associated with the design of such device, it is not believed that any device could be modified for use in other embodiment. The device of the present invention is also specifically designed. In this case, it is designed for use in connection with the removal of meconium and other materials from the oral airways and trachea region of newborn babies.

The need to remove meconium from a newborn infant is well recognized. Reference is made to an article published in (i) *Journal of Pediatrics*, December, 1974, Vol. 85, No. 6, pages 848–852 entitled "Meconium Aspiration in Infants—A Prospective Study", and (ii) Am. J. Obstet. Gynecol. 126:712, 1976 entitled "Combined Obstetric and Pediatric Approach to Prevent Meconium Aspiration Syndrome". In that latter article, meconium aspiration syndrome (MAS) is indicated to be a variety of aspiration pneumonia which occurs most frequently in term or past-term newborn infants who have passed meconium in utero. The article indicates that such infants often develop progressive respiratory failure with significant hypoxemia during the first two to three days of life. Death rates as high as 28% have been reported for MAS. Indicated in the article is what is believed to be one of the most up-to-date methods for removing meconium from the newborn infant; to wit: tracheal suction under direct laryngoscopic vision as soon as possible after the birth of the at-risk infant. Recently, intrapartum nasopharyngeal suction has been added as an additional technique. Generally, as soon as the baby's head appears on the perineum, and prior to the delivery of the shoulders, the doctor passes a suction catheter through the nares to the level of the nasopharynx and aspirates any mucus or meconium. The doctor then suctions the mouth and hypopharynx in a similar manner. Because the field into which the catheter is being passed (i.e., a baby's mouth and nose) is small, and irregular in shape, a flexible tubing is often used. Following the delivery, the doctor then with the aid of a laryngoscope shines light and visualizes the area directly above and below the vocal cords looking for meconium. If it is present it must be removed by a suction device (usually a standard endotracheal tube with an internal guide wire) as quickly as possible to try to avoid greater or deeper aspirations of this material. The current art is that the same device that suctions the mouth and nose cannot be used for the trachea because its flexibility makes the intubation process too difficult.

Because proper placement of the endotracheal tube to remove the meconium is critical, the infant is held in position and a doctor or other hospital personnel then inserts the tube which has a stiffening wire inserted therein. The stiffening wire enables the otherwise flexible tube to travel into the trachea. Once in proper position, the stiffening wire must be removed in order to allow the doctor to suck out any meconium in the trachea region. The doctor must place his mouth over the proximal end of the endotracheal tube. Then during suction he must remove the endotracheal tube and dispose of any meconium which has been sucked out. If meconium remains, he must then reinsert the tube in the trachea again with the guide wire stylet and repeat the process as often as needed until no further meconium is retrieved.

The problems with such approach are obvious. Insertion is accomplished with the laryngoscope in one hand and the endotracheal tube and stiffening wire in the other hand. After the tube is inserted, prior to mouth suction, the wire must be removed. To do this the laryngoscope must be placed down to free a hand to remove the wire. This is very awkward and has lead to the accidental removal of the endotracheal tube from the proper position in the trachea. In summary, the problems with a guide wire type intubation device are:

1. Such a device occludes the lumen of the endotracheal tube and which therefore must be removed prior to the application of suction;
2. The wire can only be removed after proper placement;
3. Removal of the wire is often clumsy and can inadvertently dislodge the endotracheal tube from the desired position;
4. The guide wire must be reinserted for reintubation which is often times required; and
5. The laryngoscope must be put aside in order to free a hand to remove stylet prior to suction.

An example of an intubation tube used in the prior art is found in U.S. Pat. No. 3,996,939. In such device, the wire or "stylet" is used in intubating the endotracheal tube, catheter or like medico-surgical tube. The stylet comprises a bendable metal rod hermetically sealed in a tubular plastic sheath such that the rod is contained in the sheath. The tube and stylet are inserted into the trachea region at which time the stylet is removed and suction is applied to the catheter.

The problem with such device is that it is structurally complex. Another problem is the time factor. Removal of meconium is considered to be an emergency procedure in which every second counts. If the infant's head turns and proper insertion cannot be made after a number of tries, the probabilities that the infant will more deeply aspirate meconium is increased. Should the stylet be removed and then proper positioning destroyed, reinsertion may be necessary in order to again achieve proper positioning. Finally, the '939 device is awkward to use as it does not permit the user to simultaneously suction the desired area while holding the laryngoscope during insertion.

Given all of these problems which are well recognized by the prior art, there is still no satisfactory answer which has evolved until the advent of the invention set forth hereinbelow.

It is therefore one object of the present invention to provide a device which can be used to clean the oral and nasal airways prior to the first breath being taken by a newborn infant so as to substantially prevent the aspiration of meconium.

It is yet a further object of the present invention to provide a device which can be easily inserted into the trachea region of a newborn infant so as to remove any meconium from that region as well.

It is yet another object of the present invention to minimize the time associated with the proper insertion of the device.

It is yet another object of the present invention to enable removal of meconium in a substantially more sanitary manner than that associated with the prior art devices.

It is yet another object of the present invention to enable the doctor, while guiding the intubation tubing, to simultaneously suck out meconium and to have a free hand to accurately direct the laryngoscope.

By the use of the device of the present invention, it is believed that a more thorough removal of meconium and other dangerous materials from the oral airways and trachea region of a newborn infant can be achieved. Further, problems caused by repeated intubation are eliminated.

BRIEF SUMMARY OF THE INVENTION

An endotracheal intubation device is disclosed which enables the user to simultaneously apply suction during the intubation process. By the use of the device of the present invention, both the upper airways as well as the trachea region can be cleaned using a single apparatus. In addition, the device of the present invention allows for suction during direct visualization of the oropharynx and larynx. This enables the more accurate application of suction to a specific region. The present invention comprises a first elongated, flexible conduit having an insertion end configured for insertion through the mouth, nose and trachea, with placement into the oro or nasopharynx, larynx or stomach and a proximal end configured for joining to a source of suction. A second elongated conduit is circumferentially disposed about the first conduit in sliding relationship therewith. The second conduit has an insertion end configured for insertion into the mouth area up to the vocal cords and grip means disposed adjacent the proximal end. The second conduit also has means for selectively shaping the second conduit into a generally arcuous configuration and retaining said second conduit as well as the first conduit in such configuration.

The novel features which are believed to be characteristic of the invention, both as to its organization and method of operation, together with further objectives and advantages thereof will be better understood from the following description considered in connection with accompanying drawings in which a presently preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a view showing the device of the present invention inserted into the trachea region;

FIG. 2 is a side plan view of the device;

FIG. 3 is a top plan view of the device;

FIG. 4 is a top plan view showing a different means for shaping the device into a specific configuration; and FIG. 5 shows the device with a different type of suction trap.

DETAILED DESCRIPTION OF THE INVENTION

Referring first to FIG. 1, one can see the device 10 of the present invention inserted into the trachea region 12 of a baby generally referred to by the numeral 14. As is shown in this FIGURE, the device 10 has passed through the mouth 16, through the oral airway 18, and into the trachea 12. While it may appear that this procedure could be easily performed, in practice it is most difficult. Generally, a highly trained nurse or physician would be responsible for inserting a similar device into the oral airway 18 and trachea 12 so as to remove meconium or other undesirable materials from such regions. The physician would, as discussed in connection with the prior art, generally hold a laryngoscope in one hand while simultaneously attempting to properly insert the intubation device with the other. This has lead to a substantial number of problems associated with the proper insertion. While insertion can be achieved with devices of the prior art, the problem is that aspiration of meconium can have a devastating effect on the well being of a newborn baby. Accordingly, time is of the essence and should proper placement not be achievable during the first few attempts, it is believed that the probabilities associated with aspiration of meconium or like materials substantially increases. Accordingly, the need exists for a device which can be easily inserted into the oral airway 16 and trachea 18 as illustrated in FIG. 1. As hereinafter discussed, the device 10 of the present invention enables this procedure to be rapidly carried out without the problems associated with the prior art. Further, the device 10 enables the physician to begin the suction process at the time of intubation without the necessity of the awkward removal of the trachea guiding stylet.

Referring now to FIGS. 2 and 3, the device 10 of the present invention is more fully illustrated. The device 10 comprises a first inner tube 20 having a distal end 22 and a proximal end 24. The first inner tube 20 is generally made of a flexible plastic material such that it can easily be bent so as to achieve the proper shape for easy insertion into the oral airways and trachea region of a newborn baby. Adjacent the distal end 22 there may be exposed a plurality of openings 28 so as to promote the ability of the tube 20 to remove meconium and other undesirable materials as hereinafter described. The proximal end 24 may have a mouthpiece attached thereto such that once the device 10 has been properly inserted, sucking on the mouthpiece will cause suction to be created at the distal end 22 thereby removing any meconium or other undesirable materials adjacent such end.

Circumferentially disposed about the first tube 20 is a second outer tube 30. Outer tube 30 is also made of a soft, generally flexible plastic material and has a distal end 32 and a proximal end 34. The distal end 32 has a tapered insertion tip configured such that it can be nontraumatically disposed up to the larynx of the newborn baby, and removed with a minimal amount of tissue damage. However, the internal diameter of the outer tube 30 and the outside diameter of the inner tube 20 are selected such that the outer tube 30 is slideably disposed about the inner tube 20. The length of the inner tube 20 is chosen such that its distal end 22 extends beyond the distal end 32 of outer tube 30.

Disposed adjacent the proximal end 34 is an outwardly extending grip member 38. This is perhaps most clearly shown with reference to FIG. 3. In the preferred embodiment, grip member 38 is comprised of two outwardly extending tab members 40. It is to understood, however, that a wide variety of other grip members are also within the scope of this invention. The specific operation of the grip member 38 will be described hereinbelow.

Again referring to FIGS. 2 and 3, one can see that the outer tube 30 has a plurality of pleats 42 formed by folds 44. This configuration represents one means for shaping the second tube 30 into a predetermined configuration such that the second tube is selectively retained in such configuration. For example, referring to FIG. 2, one can see that the outer tube 30 has a generally arcuous shape. The pleats 42 have sufficient strength such that once the tube 30 is disposed in that configuration, it will not easily be altered unless some preselected amount of effort is applied to the tube thereby changing its configuration. This ability to selectively retain the shape of the second tube necessitated by the variability in the size and shape of the upper airway anatomy enables the device 10 to be properly inserted by pre-bending the tube 30 and then inserting it into the trachea region 12. In addition, because the outer tube 30 is disposed about the inner tube 20, shaping the outer tube 30 causes the inner tube 20 to be retained in that same configuration. Note that the length of tube 20 is such that it alone extends into the trachea region 12.

In operation of the device 10 of the present invention, the outer tube 30 is disposed about the inner tube 20 such that the distal end 22 of the inner tube 20 extends beyond the distal end 32 of the outer tube 30 a predetermined distance. The doctor would then simultaneously grasp the inner tube 20 and outer tube 30 by applying pressure to the proximal end 24 against the grip member 38. The device 10 would then be bent into the desired configuration, and with the use of a laryngoscope, insertion would begin. However, because only one hand is needed to hold the device 10, the doctor can more accurately direct the laryngoscope and simultaneously apply suction during the entire intubation process. For example, as the tubes 20 and 30 are inserted and should the doctor see any meconium fluid in the mouth region, it would be sucked out. As the device 10 proceeds down the oral airways 18 into the trachea region 12, any meconium seen can also be likewise removed. Note, however, that the length and the placement of the tubes 20, 30 are such that only tube 20 enters the trachea 12. After this placement is achieved, the inner tube 20 can be slid through the outer tube 30 for deeper airway suction.

Referring now to FIG. 4, one can see an alternate embodiment of the present invention. In this embodiment, the outer tube 30 has a bendable wire 56 disposed along the length thereof. Shaping, using the bendable wire, is achieved by merely bending the outer tube 30 thereby deforming the wire 56. As discussed hereinabove, shaping the outer tube 30 would cause the inner tube 20 to achieve the same shape.

While the device 10 described hereinabove readily overcomes a number of problems associated with the prior art, the problem of the doctor accidentally sucking meconium into his own mouth is not prevented. Referring now to FIG. 5, one can see the device 10 of the present invention wherein the inner tube 20 is connected to a suction trap 46. Trap 46 is comprised of a vial 48 which has a cap 50 and a third tube 52 disposed therein. Adjacent the proximal end of tube 52 is a mouth piece 54. By sucking on mouthpiece 54, a suction would be created at the distal end 22 of the tube 20. In this manner, the problem of directly sucking meconium into the mouth of the physician is substantially prevented so that any meconium sucked up by the physician would be transferred to the trap 46. Further, trap 46 would eliminate the awkward, time consuming potentially traumatic reintubation process normally needed to dispose of the suctioned meconium. It is to be understood, however, that other forms of traps are also within the scope of this invention.

While this invention has been described with reference to specific embodiments it is to be understood, that other embodiments are also within the scope of this invention.

I claim:

1. An endotracheal intubation device which enables the user to simultaneously apply suction during the intubation process to remove meconium and other accumulated body fluids, comprising:
   a first inner elongated, flexible conduit of a greater length than a second elongated conduit and extending throughout having a smooth, tapered insertion end configured for insertion into the upper airways of a newborn baby and a proximal end configured for joining to a source of suction; and
   a second outer elongated conduit circumferentially disposed about said first conduit along the length thereof and in sliding relationship therewith, said insertion end of the first conduit extending beyond the distal end of the second conduit, said distal end of second conduit being smooth and configured for nontraumatic insertion into the mouth area, and outwardly extending grip means disposed adjacent the other end of said second conduit, said second conduit further having means for selectively shaping and retaining said second conduit substantially along its entire length into any one of an infinite different configurations, but generally of an arcuate configuration whereby shaping said second outer conduit into a selected configuration causes said first, inner conduit to be shaped and retained in a substantially congruent configuration.

2. An endotracheal intubation device according to claim 1 wherein said first conduit is joined to a suction trap.

3. An endotracheal intubation device according to claim 1 wherein said grip means comprises generally flat, outwardly extending members configured such that said first and second conduits can be gripped together in a plurality of different positions.

4. An endotracheal intubation device according to claims 1 or 2 wherein said shaping means comprises accordian-like pleats formed in said second conduit.

5. An endotracheal intubation device according to claims 1 or 2 wherein said shaping means comprises a bendable, stiffening element disposed along the length of said second conduit.

* * * * *